(12) United States Patent
Zhou et al.

(10) Patent No.: US 8,367,415 B2
(45) Date of Patent: Feb. 5, 2013

(54) SPECIFIC GENE POLYMORPHISMS IN BREAST CANCER DIAGNOSIS, PREVENTION AND TREATMENT

(75) Inventors: Juhua Zhou, Lexington, SC (US); Mitzi Nagarkatti, Columbia, SC (US); Prakash Nagarkatti, Columbia, SC (US)

(73) Assignee: University of South Carolina, Columbia, SC (US)

( * ) Notice: Subject to any disclaimer, the term of this patent is extended or adjusted under 35 U.S.C. 154(b) by 323 days.

(21) Appl. No.: 12/555,128

(22) Filed: Sep. 8, 2009

(65) Prior Publication Data

US 2010/0063382 A1    Mar. 11, 2010

Related U.S. Application Data

(60) Provisional application No. 61/191,079, filed on Sep. 5, 2008.

(51) Int. Cl.
*C12Q 1/68* (2006.01)
*G01N 33/48* (2006.01)

(52) U.S. Cl. ............ 436/64; 436/63; 436/87; 436/94; 435/6.1; 435/6.11; 435/6.12; 435/6.14; 435/6.17; 536/23.1

(58) Field of Classification Search ............ 436/63, 436/64, 86, 87, 94; 422/430; 435/6.1, 6.11, 435/6.12, 6.14, 6.17, 810; 536/23.1
See application file for complete search history.

(56) References Cited

U.S. PATENT DOCUMENTS

2002/0081598 A1*  6/2002  Evans et al. .............. 435/6
2007/0166738 A1*  7/2007  Cox et al. ................. 435/6

FOREIGN PATENT DOCUMENTS

WO    2008/077165    *  7/2008

OTHER PUBLICATIONS

Msyer et al. Journal of Cancer Research and Clinical Oncology, vol. 134, Apr. 26, 2008, pp. 1229-1235.*

* cited by examiner

*Primary Examiner* — Maureen Wallenhorst
(74) *Attorney, Agent, or Firm* — Dority & Manning, P.A.

(57) ABSTRACT

A method for detecting a predisposition to breast cancer in a subject is provided. The method includes detecting in a biological sample from the subject one or more polymorphisms in the sequence of CD44 gene. The presence of one or more polymorphisms in the sequence of CD44 gene indicates that the subject has a predisposition for developing breast cancer.

12 Claims, 6 Drawing Sheets

Figure 1

```
>S703779.USU-1-M13R
GGAGTCTGTCCTAAACTGAACTTATTACTGTCTCCAAATTATTTATGCAAAAGAATCTAACATTTCTGTTTCTT
CCCATAGATTTGAATATAACCTGCCGCTTTGCAGGTGTATTCCACGTGGAGAAAAATGGTCGCTACAGCATCT
CTCGGACGGAGGCCGCTGACCTCTGCAAGGCTTTCAATAGCACCTTGCCCACAATGGCCCAGATGGAGAAAG
CTCTGAGCATCGGATTTGAGACCTGCAGGTAAGAGACCAGCACCCGACCACTGGGGAAAGCT
```

Figure 2

```
>gnl|dbSNP|rs4756195
rs=4756195|pos=825|len=1025|taxid=9606|mol="genomic"|class=1|alleles="A/G"|build=126
Length=1025
 Score = 350 bits (189), Expect = 1e-93, Identities = 191/192 (99%), Gaps = 0/192 (0%),
Strand=Plus/Plus Query  61   CATTTCTGTTTCTTCCCATAGATTTGAATATAACCTGCCGCTTTGCAGGTGTATTCCACG  120
Sbjct  894  .......A....................................................  953
```

Figure 3

```
>S702700.USC-12-M13R
GGAGTCTGTCCTAAACTGAACTTATTACTGTCTCCAAATTATTTATGCAAAAGAATCTAACATTTCTGTTTCTTCCCAT
AGATTTGAATATAACCTGCCGCTTTGCAGGTGTATTCCACGTGGAGAAAAATGGTCGCTACAGCATCTCTCGGACGGGG
GCCGCTGACCTCTGCAAGGCTTTCAATAGCACCTTGCCCACAATGGCCCAGATGGAGAAAGCTCTGAGCATCGGATTTG
AGACCTGCAGGTAAGAGACCAGCACCCGACCACTGGGGAAAGCT

>gnl|dbSNP|rs4756195
rs=4756195|pos=825|len=1025|taxid=9606|mol="genomic"|class=1|alleles="A/G"|build=126Lengt
h=1025 Score =  344 bits (186),  Expect = 6e-92 Identities = 190/192 (98%), Gaps = 0/192
(0%) Strand=Plus/Plus Query   61    CATTTCTGTTTCTTCCCATAGATTTGAATATAACCTGCCGCTTTGCAGGTGTATTCCACG   120
Sbjct   894   .......A....................................................   953

Query   121   TGGAGAAAAATGGTCGCTACAGCATCTCTCGGACGGGGGCCGCTGACCTCTGCAAGGCTT   180
Sbjct   954   ....................................A.......................   1013
```

Figure 4

```
>S702700.USC-24-M13R
GGAGTCTGTCCTAAACTGAACTTATTACTGTCTCCAAATTATTTATGCAAAAGAATCTAACATTTCTGTTTCTTCCCAT
AGATTTGAATATAACCTGCCACTTTGCAGGTGTATTCCACGTGGAGAAAAATGGTCGCTACAGCATCTCTCGGACGGAG
GCCGCTGACCTCTGCAAGGCTTTCAATAGCACCTTGTCCACAATGGCCCAGATGGAGAAAGCTCTGAGCATCGGATTTG
AGACCTGCAGGTAAGAGACCAGCACCCGACCACTGGGGAAAGCT

>gnl|dbSNP|rs4756196
rs=4756196|pos=825|len=1025|taxid=9606|mol="genomic"|class=1|alleles="A/G"|build=126Lengt
h=1025 Score =  483 bits (261),  Expect = 1e-133 Identities = 265/268 (98%), Gaps = 0/268
(0%) Strand=Plus/Plus Query    61    CATTTCTGTTTCTTCCCATAGATTTGAATATAACCTGCCACTTTGCAGGTGTATTCCACG    120
Sbjct    818   .......A.............................G....................    877

Query    121   TGGAGAAAAATGGTCGCTACAGCATCTCTCGGACGGAGGCCGCTGACCTCTGCAAGGCTT    180
Sbjct    878   ............................................................    937

Query    181   TCAATAGCACCTTGTCCACAATGGCCCAGATGGAGAAAGCTCTGAGCATCGGATTTGAGA    240
Sbjct    938   ..............C.............................................    997
```

Figure 5

```
>S702700.USC-26-M13R
GGAGTCTGTCCTAAACTGAACTTATTACTGTCTCCAAATTATTTATGCAAAAGAGTCTAACATTTCTGTTTCTTCCCAT
AGATTTGAATATAACCTGCCGCTTTGCAGGTGTATTCCACGTGGAGAAAAATGGTCGCTACAGCATCTCTCGGACGGAG
GCCGCCGACCTCTGCAAGGCTTTCAATAGCACCTTGCCCACAATGGCCCAGATGGAGAAAGCTCTGAGCATCGGATTCG
AGACCTGCAGGTAAGAGACCAGCACCCGACCACTGGGGAAAGCT

>gnl|dbSNP|rs4756196
rs=4756196|pos=825|len=1025|taxid=9606|mol="genomic"|class=1|alleles="A/G"|build=126Lengt
h=1025 Score =  477 bits (258),  Expect = 6e-132 Identities = 264/268 (98%), Gaps = 0/268
(0%) Strand=Plus/Plus Query   1    GGAGTCTGTCCTAAACTGAACTTATTACTGTCTCCAAATTATTTATGCAAAAGAGTCTAA   60
Sbjct   758  .................................................A.....    817

Query   61   CATTTCTGTTTCTTCCCATAGATTTGAATATAACCTGCCGCTTTGCAGGTGTATTCCACG   120
Sbjct   818  .......A....................................................   877

Query   121  TGGAGAAAAATGGTCGCTACAGCATCTCTCGGACGGAGGCCGCCGACCTCTGCAAGGCTT   180
Sbjct   878  ..........................................T................   937

Query   181  TCAATAGCACCTTGCCCACAATGGCCCAGATGGAGAAAGCTCTGAGCATCGGATTCGAGA   240
Sbjct   938  ....................................................T....   997
```

Note:
Group I patients: the patients contained only unique CD44 exon2+14A→G polymorphism and the average age is 58±2 when the patients were diagnosed with breast cancer. Group II patients: the patients contained additional CD44 polymorphisms in CD44 exon2 coding sequence and the average age is 43±2 when the patients were diagnosed with breast cancer.

SPECIFIC GENE POLYMORPHISMS IN BREAST CANCER DIAGNOSIS, PREVENTION AND TREATMENT

CROSS REFERENCE TO RELATED APPLICATION

The present application claims is based on and claims priority to U.S. Provisional Application Ser. No. 61/191,079, filed Sep. 5, 2008, which is incorporated by reference herein in its entirety.

GOVERNMENT SUPPORT CLAUSE

This invention was made with government support under 5R01A/05373-06 awarded by the National Institutes of Health. Therefore, the government has certain rights in the invention.

BACKGROUND

Breast cancer is a leading cause of cancer-related deaths in women in the United States and worldwide. Inherited genetic variations, or gene polymorphisms, are viewed as major factors in breast cancer prevalence.

A number of breast cancer susceptibility genes have been identified. The two most important breast cancer susceptibility genes, BRCA1 and BRCA2, accounted for approximately 15% of breast cancer cases due to inherited mutations or alterations. However, BRCA1 and BRCA2 mutations are present in far less than 1% of the general population. In addition to BRCA1 and BRCA2, five other genes, TP53, PTEN, LKB1, ATM and CHEK2, are also well established breast cancer susceptibility genes. The proportion of breast cancer in the general population explained by these gene mutations is very small. It is estimated that all the currently known breast cancer susceptibility genes accounts for less than 25% of the familial aggregation of breast cancer. The evidence to date strongly suggests that the majority of the familial clustering of breast cancer is unexplained and other breast cancer susceptibility genes still remain to be identified. The identification of new genes could make a major impact in risk prediction.

CD44 is a cell surface transmembrane glycoprotein, encoded by a single gene. Transcripts for CD44 gene undergo complex alternative splicing that results in many functionally distinct isoforms. Recent experimental and clinical evidence shows that CD44 and its interaction with hyaluronan may regulate breast cancer cell proliferation, migration, and invasion, as well as tumor-associated angiogenesis and are correlated with patient survival. Thus, CD44 polymorphisms play an important role in breast cancer development.

SUMMARY

Objects and advantages of the invention will be set forth in part in the following description, or may be obvious from the description, or may be learned through the practice of the invention.

In accordance with certain embodiments of the present disclosure, a method for detecting a predisposition to breast cancer in a subject is provided. The method comprises detecting in a biological sample from the subject one or more polymorphisms in the sequence of CD44 gene. The presence of one or more polymorphisms in the sequence of CD44 gene indicates that the subject has a predisposition for developing breast cancer.

In still another embodiment of the present disclosure, a diagnostic kit for identifying a predisposition to breast cancer in a subject is provided. The kit comprises packaging material and means for amplifying at least a region of a CD44 gene from a biological sample of a subject.

Other features and aspects of the present disclosure are discussed in greater detail below.

BRIEF DESCRIPTION OF THE DRAWINGS

A full and enabling disclosure, including the best mode thereof, directed to one of ordinary skill in the art, is set forth more particularly in the remainder of the specification, which makes reference to the appended figures in which:

FIG. 1 is the sequence of a cloned PCR product from a PBMC sample of breast cancer patient (SEQ ID NO: 3).

FIG. 2 is a single nucleotide polymorphism analysis of S703779.USU-1-M13R clone (polymorphic change in bold). FIG. 2 discloses residues 61-120 of SEQ ID NO: 3 and SEQ ID NO: 4, respectively, in order of appearance.

FIG. 3 is the CD44 polymorphism in the CD44 exon2 coding region from a breast cancer patient A (polymorphic change in CD44 exon2 coding sequence in bold). FIG. 3 discloses SEQ ID NO: 5, residues 61-180 of SEQ ID NO: 5 and SEQ ID NO: 6, respectively, in order of appearance.

FIG. 4 is the CD44 polymorphism in the CD44 exon2 coding region from a breast cancer patient B (polymorphic change in CD44 exon2 coding sequence in bold). FIG. 4 discloses SEQ ID NO: 7, residues 61-240 of SEQ ID NO: 7, and SEQ ID NO: 8, respectively, in order of appearance.

FIG. 5 is the CD44 polymorphism in the CD44 exon2 coding region from a breast cancer patient C (polymorphic change in CD44 exon2 coding sequence in bold), FIG. 5 discloses SEQ ID NO: 9, residues 1-240 of SEQ ID NO: 9, and SEQ ID NO: 10, respectively, in order of appearance.

Figure 6:
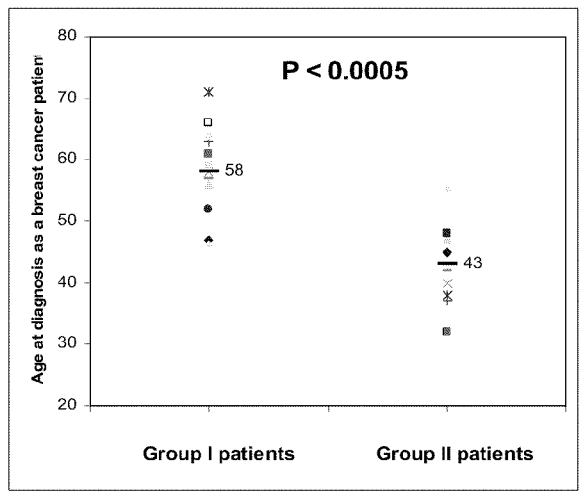
FIG. 6 illustrates an association of CD44 polymorphisms and patient age at breast cancer diagnosis.

Table 1 is a summary of unique CD44 polymorphism (Ex2+14 A>G) in breast cancer patients.

Table 2 is a comparison of unique CD44 polymorphism (Ex2+14 A>G) between Caucasian breast cancer patients and Caucasian normal donors.

Table 3 is a summary of additional CD44 polymorphisms in CD44 exon2 coding sequence in breast cancer patients.

DETAILED DESCRIPTION

Reference now will be made in detail to various embodiments of the disclosure, one or more examples of which are set forth below. Each example is provided by way of explanation of the disclosure, not limitation of the disclosure. In fact, it will be apparent to those skilled in the art that various modifications and variations can be made in the present disclosure without departing from the scope or spirit of the disclosure. For instance, features illustrated or described as part of one embodiment, can be used on another embodiment to yield a still further embodiment. Thus, it is intended that the present disclosure covers such modifications and variations as come within the scope of the appended claims and their equivalents.

Generally, the present disclosure provides a method of testing a subject to determine if the subject has a predisposition for developing breast cancer.

The methods of the present disclosure provide that either healthy subjects and/or subjects at risk (after primary breast cancer) are screened by obtaining various patient-derived materials such as tissue samples or blood (normally blood, such as peripheral blood mononuclear cells, including lymphocytes or a monocytes), which is then examined using methods known to those in the art for the presence of single-nucleotide polymorphism (also referred to herein generally as polymorphisms). The tissue sample can include, but are not limited to, blood, mouth brush secretions, other secretions and other tissues.

The methods which are used to detect the presence of the polymorphisms include, but are not limited to methods known in the art for amplifying or sequencing the one or more polymorphisms and detecting the one or more polymorphisms or sequences thereof. Methods can include methods which require the use of primers, as further described herein. The methods can include one or more of polymerase chain reaction, ligase chain reaction, restriction digestion, direct sequencing, nucleic acid amplification, microchips, hybridization or immunoassays. The methods described herein can further include a visualization method of the breast including one or more of MRI, mammography, or ultrasonography on the subject to detect breast cancer.

The present disclosure describes CD44 polymorphisms as a good marker in breast cancer disease prediction and diagnosis. In particular, the present disclosure reveals patients with breast cancer have a significantly increased frequency of CD44 Ex2+14 A>G polymorphism. The predisposition may be an inherited predisposition, as described further herein.

The present disclosure also provides a diagnostic kit for identifying a predisposition to breast cancer, including packaging material and one or more different polynucleotides capable of amplifying at least a region of a CD44 gene. In some embodiments of the present disclosure, the amplified region includes CD44 Ex2+14 A>G polymorphism. The kit may also contain instructions, e.g., instructions for using the kit to identify a predisposition to breast cancer, including instructions for performing a visualization method of the breast. In addition, the kit can allow for the ability to sequence at least a region of a CD44 gene from a biological sample of a user of the diagnostic kit. For instance, the kit can include packaging to send a biological sample to be sequenced by a DNA sequencer, or another method, as further described above.

(1) Unique CD44 Polymorphism in Breast Cancer Patients:

Since CD44 polymorphisms are present in breast cancer patients and are associated with breast cancer development, the direct nucleotide sequencing strategy was used to analyze CD44 polymorphisms in breast cancer patients. A unique polymorphism in the boundary region between CD44 exon2 and its upstream intron was identified in breast cancer patients, which is located in the upstream intron of CD44 exon2 (FIGS. 1 and 2). The polymorphic change is A→G, and its position is +14 from CD44 exon2. This unique CD44 polymorphism was designated as the Ex2+14 A>G polymorphism. The Caucasian breast cancer patients had a significantly higher frequency of this unique polymorphism than Asian breast cancer patients (Table 1), which may be associated with the fact that white women have a higher incidence and death rate from breast cancer than women of other racial and ethnic groups. As compared with the Caucasian normal donors, the Caucasian patients with breast cancer have a significantly increased frequency of CD44 Ex2+14 A>G polymorphism (Table 2). These results indicated that the identified CD44 polymorphism plays an important role in breast cancer development.

(2) Polymorphisms in CD44 Exon2 Coding Sequence in Breast Cancer Patients:

CD44 is a major cell surface receptor for hyaluronan (HA), a component of the extracellular matrix. Many of the functions of CD44 in cell adhesion and activation can be attributed to CD44 binding. Exon2 is critical for CD44 binding to HA. Thus, there is interest in understanding the polymorphisms in the CD44 exon2 coding region and their role in breast cancer development. The direct nucleotide sequencing analysis indicated that different polymorphic changes in the CD44 exon2 coding region were identified in different breast cancer patients (FIGS. 3, 4 and 5). Therefore, except the unique CD44 Ex2+14 A>G polymorphism in the boundary region between CD44 exon2 and its upstream intron, the additional polymorphisms in the CD44 exon2 coding sequence are also present in breast cancer patients. Thus, the breast cancer patients were divided into two groups: (1) Group I patients: the patients contained only unique CD44 Ex2+14 A>G polymorphism and (2) Group II patients: the patients contained the additional CD44 polymorphisms in CD44 exon2 coding sequence.

Caucasian breast cancer patients had a significantly higher frequency of the polymorphisms in the CD44 exon2 coding sequence than Asian breast cancer patients (Table 3). No polymorphisms in the CD44 exon2 coding sequence have been identified in elderly Caucasian normal donors. The incidence and death rates from breast cancer are lower among women of other racial and ethnic groups than among white and African-American women, indicating that the polymorphisms in the CD44 exon2 coding sequence play an important role in breast cancer development.

(3) Relationship Between CD44 Polymorphisms and Breast Cancer Development:

As shown above, Caucasian breast cancer patients have a significantly increased frequency of the unique CD44 Ex2+14 A>G polymorphism in the boundary region between CD44 exon2 and its upstream intron than Caucasian normal donors (Table 2), indicating that this unique CD44 polymorphism plays an important role in breast cancer development. The additional polymorphisms in CD44 exon2 coding sequence have been identified only in breast cancer patients (FIGS. 3, 4 and 5; Table 3), but not in elderly Caucasian normal donors. Therefore, understanding the clinical significance of CD44 polymorphisms in breast cancer development is important. Mann-Whitney U test analysis shows that the patients containing the additional CD44 polymorphisms in CD44 exon2 coding sequence had breast cancer disease at earlier stage, which is statistically significant (FIG. 6), indicating that CD44 polymorphism may play role in breast cancer disease development.

The following examples are meant to illustrate the disclosure described herein and are not intended to limit the scope of this disclosure.

EXAMPLES

Technology for CD44 Polymorphism Analysis

Step 1: Obtain normal cells such as peripheral blood mononuclear cells (PBMC) from human subjects.

Step 2: Isolate genomic DNA samples from normal cell samples.

Step 3: Use polymerase chain reaction (PCR) method to amplify CD44 exon2 region sequences including the CD44 exon2 sequence and the boundary sequences between exon2 and upstream intron and between exon2 and downstream intron from genomic DNA samples in the presence of the forward primer (5'-GGAGTCTGTCCTAAACTGA ACTTATTACTG-3' (SEQ ID NO: 1)) and the reverse primer (5'-AGCTTTCCCCAGTGGTCGGGTGC TGGTCTC-3' (SEQ ID NO: 2)).

Step 4: Clone PCR products of CD44 exon2 region sequences using a cloning vector such as pCR2.1 TOPO from Invitrogen.

Step 5: Transform the cloned PCR products into bacterial competent cells such as TOP10 cells from Invitrogen.

Step 6: Isolate plasmid DNA samples containing the cloned CD44 exon2 region sequences using plasmid DNA preparation kit such as QIAprep spin miniprep kit from QIAGEN.

Step 7: Sequence the plasmid DNA samples containing the cloned CD44 exon2 region sequences using automated DNA sequencer.

Step 8: Analyze the polymorphic changes in CD44 exon2 region including CD44 exon2 coding sequence and the adjacent intron sequences.

Step 9: Use the information about CD44 polymorphisms to prevent, predict and diagnose breast cancer.

It has been well documented that the two most important breast cancer susceptibility genes, BRCA1 and BRCA2, accounted for approximately 15% of breast cancer cases due to inherited mutations or alterations. However, BRCA1 and BRCA2 mutations are present in far less than 1% of the general population. It is estimated that all the currently known breast cancer susceptibility genes accounts for less than 25% of the familial aggregation of breast cancer. Our data demonstrated that CD44 gene polymorphisms/variations may account for 80% of breast cancer cases. Thus, CD44 polymorphisms will be a good marker in breast cancer disease prediction and diagnosis. The technique of CD44 polymorphism analysis used in breast cancer patients is feasible and reliable so that CD44 polymorphism analysis has a great potential in clinical prevention, diagnosis and treatment for breast cancer patients.

Early diagnosis of cancer diseases is a big challenge in effective cancer treatment. Genetic screen of CD44 polymorphisms in breast cancer patients will provide a novel platform for cancer prevention and early cancer disease diagnosis, which will be of benefit to the effective clinical treatment of breast cancer disease.

In the interest of brevity and conciseness, any ranges of values set forth in this specification are to be construed as written description support for claims reciting any sub-ranges having endpoints which are whole number values within the specified range in question. By way of a hypothetical illustrative example, a disclosure in this specification of a range of 1-5 shall be considered to support claims to any of the following sub-ranges: 1-4; 1-3; 1-2; 2-5; 2-4; 2-3; 3-5; 3-4; and 4-5.

These and other modifications and variations to the present disclosure can be practiced by those of ordinary skill in the art, without departing from the spirit and scope of the present disclosure, which is more particularly set forth in the appended claims. In addition, it should be understood that aspects of the various embodiments can be interchanged both in whole or in part. Furthermore, those of ordinary skill in the art will appreciate that the foregoing description is by way of example only, and is not intended to limit the disclosure so as further described in such appended claims.

TABLE 1

|  | Female breast cancer patients | |
| --- | --- | --- |
|  | Caucasian | Asian |
| Number of patients containing unique CD44 polymorphism | 33 | 12 |
| Number of patients without unique CD44 polymorphism | 8 | 11 |
| Total number of patients analyzed | 41 | 23 |
| Percentage of patients containing unique CD44 polymorphism (%) | 80 | 52 |

Note:
Statistical analysis indicated that Caucasian female breast cancer patients had a significant higher percentage of the patients containing unique CD44 Ex2 + 14 A > G polymorphism than Asian female breast cancer patients (Odds ratio, 3.78; 95% confidence intervals, 1.23-11.65; $p < 0.05$).

TABLE 2

|  | Caucasian population | |
| --- | --- | --- |
|  | Cancer patient | Normal donor |
| Number of subjects containing unique CD44 polymorphism | 33 | 4 |
| Number of subjects without unique CD44 polymorphism | 8 | 5 |
| Total number of subjects analyzed | 41 | 9 |
| Percentage of subjects containing unique CD44 polymorphism (%) | 80 | 44 |

Note:
Statistical analysis indicated that Caucasian female breast cancer patients had a significant higher percentage of the patients containing unique CD44 Ex2 + 14 A > G polymorphism than Caucasian normal donors (Odds ratio, 5.16; 95% confidence intervals, 1.12-23.69; $p < 0.05$).

TABLE 3

|  | Female breast cancer patients | |
| --- | --- | --- |
|  | Caucasian | Asian |
| Number of patients containing unique CD44 polymorphism only | 16 | 7 |
| Number of patients containing additional CD44 polymorphisms | 17 | 2 |
| Total number of patients analyzed | 33 | 9 |
| Percentage of patients containing additional CD44 polymorphisms (%) | 52 | 22 |

Note:
Statistical analysis indicated that Caucasian female breast cancer patients had a significant higher percentage of the patients containing additional CD44 polymorphisms than Asian female breast cancer patients (Odds ratio, 3.72; 95% confidence intervals, 0.67-20.63).

What is claimed:

1. A method for detecting a predisposition to breast cancer in a subject, comprising:

obtaining a biological sample from a subject;

isolating genomic DNA from the biological sample;

amplifying CD44 exon2 region sequences including the CD44 exon2 sequence and boundary sequences between exon2 and upstream intron and between exon2 and downstream intron from the genomic DNA in the presence of a forward primer SEQ ID NO: 1 and a reverse primer SEQ ID NO: 2 to form amplification products; and detecting in the amplification products one or more polymorphisms, wherein the presence of one or more polymorphisms in the sequence of CD44 exon2 gene indicates that the subject has a predisposition for developing breast cancer.

2. The method as in claim 1, wherein the subject is a human.

3. The method as in claim 1, wherein the biological sample comprises blood.

4. The method as in claim 1, wherein the biological sample comprises peripheral blood mononuclear cells.

5. The method as in claim 1, further comprising performing a visualization method of a breast of the subject comprising one or more of MRI, mammography, or ultrasonography to detect breast cancer.

6. The method as in claim 1, wherein the predisposition is an inherited predisposition.

7. The method as in claim 1, wherein the one or more polymorphisms in the sequence of CD44 gene comprises Ex2+14 A>G.

8. The method as in claim 1, further comprising cloning the amplification products to form cloned PCR products.

9. The method as in claim 8, further comprising transforming the cloned PCR products into bacterial competent cells to develop plasmid DNA samples containing the cloned PCR products.

10. The method as in claim 9, further comprising isolating the plasmid DNA samples containing the cloned PCR products.

11. The method as in claim 10, further comprising sequencing the plasmid DNA samples.

12. The method as in claim 11, further comprising analyzing the polymorphisms and the adjacent intron sequences.

* * * * *

SEQUENCE LISTING

<160> NUMBER OF SEQ ID NOS: 10

<210> SEQ ID NO 1
<211> LENGTH: 30

-continued

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
ggagtctgtc ctaaactgaa cttattactg                                          30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
agctttcccc agtggtcggg tgctggtctc                                          30

<210> SEQ ID NO 3
<211> LENGTH: 281
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
ggagtctgtc ctaaactgaa cttattactg tctccaaatt atttatgcaa aagaatctaa         60
catttctgtt tcttcccata gatttgaata taacctgccg ctttgcaggt gtattccacg        120
tggagaaaaa tggtcgctac agcatctctc ggacggaggc cgctgacctc tgcaaggctt        180
tcaatagcac cttgcccaca atggcccaga tggagaaagc tctgagcatc ggatttgaga        240
cctgcaggta agagaccagc acccgaccac tggggaaagc t                            281

<210> SEQ ID NO 4
<211> LENGTH: 60
<212> TYPE: DNA
<213> ORGANISM: Homo sapiens

<400> SEQUENCE: 4
catttctatt tcttcccata gatttgaata taacctgccg ctttgcaggt gtattccacg         60

<210> SEQ ID NO 5
<211> LENGTH: 281
<212> TYPE: DNA
<213> ORGANISM: Homo sapiens

<400> SEQUENCE: 5
ggagtctgtc ctaaactgaa cttattactg tctccaaatt atttatgcaa aagaatctaa         60
catttctgtt tcttcccata gatttgaata taacctgccg ctttgcaggt gtattccacg        120
tggagaaaaa tggtcgctac agcatctctc ggacgggggc cgctgacctc tgcaaggctt        180
tcaatagcac cttgcccaca atggcccaga tggagaaagc tctgagcatc ggatttgaga        240
cctgcaggta agagaccagc acccgaccac tggggaaagc t                            281

<210> SEQ ID NO 6
<211> LENGTH: 120
<212> TYPE: DNA
<213> ORGANISM: Homo sapiens

<400> SEQUENCE: 6
```

```
catttctatt tcttcccata gatttgaata taacctgccg ctttgcaggt gtattccacg    60
tggagaaaaa tggtcgctac agcatctctc ggacggaggc cgctgacctc tgcaaggctt   120

<210> SEQ ID NO 7
<211> LENGTH: 281
<212> TYPE: DNA
<213> ORGANISM: Homo sapiens

<400> SEQUENCE: 7
ggagtctgtc ctaaactgaa cttattactg tctccaaatt atttatgcaa aagaatctaa    60
catttctgtt tcttcccata gatttgaata taacctgcca ctttgcaggt gtattccacg   120
tggagaaaaa tggtcgctac agcatctctc ggacggaggc cgctgacctc tgcaaggctt   180
tcaatagcac cttgtccaca atggcccaga tggagaaagc tctgagcatc ggatttgaga   240
cctgcaggta agagaccagc acccgaccac tggggaaagc t                      281

<210> SEQ ID NO 8
<211> LENGTH: 180
<212> TYPE: DNA
<213> ORGANISM: Homo sapiens

<400> SEQUENCE: 8
catttctatt tcttcccata gatttgaata taacctgccg ctttgcaggt gtattccacg    60
tggagaaaaa tggtcgctac agcatctctc ggacggaggc cgctgacctc tgcaaggctt   120
tcaatagcac cttgcccaca atggcccaga tggagaaagc tctgagcatc ggatttgaga   180

<210> SEQ ID NO 9
<211> LENGTH: 281
<212> TYPE: DNA
<213> ORGANISM: Homo sapiens

<400> SEQUENCE: 9
ggagtctgtc ctaaactgaa cttattactg tctccaaatt atttatgcaa aagagtctaa    60
catttctgtt tcttcccata gatttgaata taacctgccg ctttgcaggt gtattccacg   120
tggagaaaaa tggtcgctac agcatctctc ggacggaggc cgccgacctc tgcaaggctt   180
tcaatagcac cttgcccaca atggcccaga tggagaaagc tctgagcatc ggattcgaga   240
cctgcaggta agagaccagc acccgaccac tggggaaagc t                      281

<210> SEQ ID NO 10
<211> LENGTH: 240
<212> TYPE: DNA
<213> ORGANISM: Homo sapiens

<400> SEQUENCE: 10
ggagtctgtc ctaaactgaa cttattactg tctccaaatt atttatgcaa aagaatctaa    60
catttctatt tcttcccata gatttgaata taacctgccg ctttgcaggt gtattccacg   120
tggagaaaaa tggtcgctac agcatctctc ggacggaggc cgctgacctc tgcaaggctt   180
tcaatagcac cttgcccaca atggcccaga tggagaaagc tctgagcatc ggatttgaga   240
```